United States Patent [19]

Suetsugu et al.

[11] Patent Number: 5,767,158
[45] Date of Patent: Jun. 16, 1998

[54] ENDERMIC LINIMENT

[75] Inventors: Masaru Suetsugu; Satoshi Shinojima; Okihiko Sakamoto; Masayuki Asaike; Yuki Shibata; Rumiko Kaku; Tsuneo Suehiro, all of Yokohama, Japan

[73] Assignee: Shiseido Co., Ltd., Tokyo, Japan

[21] Appl. No.: 600,491

[22] Filed: Feb. 13, 1996

[30]        Foreign Application Priority Data

Feb. 17, 1995 [JP] Japan ..................... 7-53540

[51] Int. Cl.⁶ ................. A61K 31/195; A61K 31/66
[52] U.S. Cl. ................. 514/563; 514/114; 514/564; 514/567
[58] Field of Search ..................... 514/119, 563, 514/564, 567, 615, 621, 622, 628, 630, 649, 114, 620

[56]             References Cited

FOREIGN PATENT DOCUMENTS 0356119  2/1990  European Pat. Off. .
A2702959 9/1994  France .

OTHER PUBLICATIONS

Patent Abstracts of Japan, vol. 9, No. 78, Apr. 6, 1985.

Chemical Abstracts, vol. 120, No. 26, 1994, abstract No. 330821n.

Chemical Abstracts, vol. 121, No. 16, 1994, abstract No. 186798m.

Chemical Abstracts, vol. 122, No. 4, 1995, abstract No. 38550e.

*Primary Examiner*—Phyllis G. Spivack
*Attorney, Agent, or Firm*—Townsend & Banta

[57]            ABSTRACT

An endermic liniment containing at least one type of phenylalanine compound, and/or its salt, is disclosed. This endermic liniment has a melanin production suppression effect and is superior in terms of its skin whitening effect as in preventing and/or improving chloasma, freckles and pigmentation in the skin after sunburn. It is also stable and highly safe.

2 Claims, No Drawings

ENDERMIC LINIMENT

FIELD OF THE INVENTION

The present invention relates to an endermic liniment which has a melanin generation suppression action, is superior in skin whitening effects such as preventing chloasma, freckles and pigmentation after sunburn, and is also stable and highly safe.

BACKGROUND OF THE INVENTION

The mechanism of the development of chloasma, freckles and pigmentation after sunburn, although there are some unknown details, is generally believed to be the formation of melanin pigment due to hormonal abnormalities or ultraviolet light stimulation from sunlight followed by abnormal deposition of this pigment in the skin. Treatments for such chloasma, freckles and pigmentation after sunburn include a method which comprises administration of a large amount of a melanin generation suppressing substance such as vitamin C, a method which comprises injection of glutathione and such, and a method which comprises local application of kojic acid, cysteine and such in an ointment, cream or lotion form.

In Europe and the USA, hydroquinone preparations are used as medicinal drugs. In addition, various endermic liniments including the endermic liniments containing a β-branched phenylalanine derivative(s) (Japanese unexamined patent publication Tokkai Hei 6-32727), an α-branched tyrosine derivative(s) (Tokkai Hei 6-128203), a phenylalaninol derivative(s) or a tyrosinol derivative(s) (Tokkai Hei 6-227958) are known.

However, these compounds, except for hydroquinone, manifest their effects very slowly and, therefore, they do not have an adequate whitening effect. On the other hand, hydroquinone is recognized for its effects, but general use of it is limited due to safety problems (irritation and sensitization) with this substance.

Based on these circumstances, the inventors carried out earnest research and completed the present invention by discovering that phenylalanine derivatives with specific structures and their salts manifest a whitening effect more pronounced than that of hydroquinone.

SUMMARY OF THE INVENTION

The present invention is an endermic liniment containing at least one type of phenylalanine derivative represented by the following general formula:

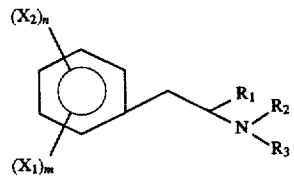

In this formula, $X_1$ denotes a hydrogen atom, hydroxyl group, methoxyl group, ethoxyl group, acetyloxyl group, iodine atom, bromine atom, chlorine atom, fluorine atom, phosphoxy group, dimethylphosphoxy group, benzyloxyl group or benzyloxycarbonyloxyl group. $X_2$ denotes a hydroxyl group, methoxyl group, ethoxyl group, acetyloxyl group, iodine atom, bromine atom, chlorine atom, fluorine atom, phosphoxy group, dimethylphosphoxy group, benzyloxyl group or benzyloxycarbonyloxyl group, and m and n denote natural numbers where $m+n \leq 5$. $R_1$ denotes a carboxyl, alkoxycarbonyl, benzyloxycarbonyl, carbamoyl, alkylcarbamoyl, naphthylcarbamoyl or hidrazinocarbonyl group. $R_2$ denotes a hydrogen atom or an alkyl, alkylcarbonyl, alkyloxycarbonyl, benzyloxycarbonyl, benzoyl, substituted benzoyl or fluorenylmethyloxycarbonyl group. $R_3$ denotes a hydrogen atom or an alkyl group. However, tyrosine and 3-methoxy-L-tyrosine are excluded.

The present invention is described in detail below.

DETAILED DESCRIPTION OF THE INVENTION

The phenylalanine derivatives and their salts pertaining to the present invention are prior art substances and they are synthesized using a conventional method by using phenylalanine or tyrosine as the starting substance, or they are readily available commercially from SIGMA, Aldrich and such.

The aforementioned compounds of the present invention, if desired, can be made into inorganic acid salts using hydrochloric acid, sulfuric acid, phosphoric acid, hydrobromic acid, etc. and organic acid salts using acetic acid, lactic acid, maleic acid, fumaric acid, tartaric acid, citric acid, methanesulfonic acid, p-toluenesulfonic acid, etc., or into inorganic salts including sodium salt, potassium salt, ammonium salt, magnesium salt and calcium salt and organic salts including monoethanol amine, diethanol amine, triethanol amine and dicyclohexyl amine.

Specific substance names include N-benzyloxycarbonyl-L-tyrosine, N-benzyloxycarbonyl-D-tyrosine, N-benzoyl-L-tyrosine, N-benzoyl-D-tyrosine, N-(p-methoxybenzoyl)-L-tyrosine, N-(p-methoxybenzoyl)-D-tyrosine, N-(p-hydroxybenzoyl)-L-tyrosine, N-(p-hydroxybenzoyl)-D-tyrosine, O-benzyloxycarbonyl-L-tyrosine, N-benzyloxycarbonyl-L-tyrosine hydrazide, N-acetyl-L-tyrosine, N-acetyl-L-tyrosine ethyl ester, N-acetyl-L-tyrosine hydrazide, N-acetyl-L-tyrosine amide, 4-methoxy-L-phenylalanine, 4-methoxy-L-phenylalanine hydrochloride, 4-methoxy-DL-phenylalanine, N-benzyloxycarbonyl-O-benzyl-L-tyrosine, O-benzyl-L-tyrosine, O-phospho-L-tyrosine, O-phospho-DL-tyrosine, O-phospho-D-tyrosine, L-tyrosine β-naphthyl amide, N-tert-butoxycarbonyl-L-3,4-dihydroxyphenylalanine, N-tert-butoxycarbonyl-O-acetyl-L-tyrosine, N-tert-butoxycarbonyl-O-acetyl-D-tyrosine, N-tert-butoxycarbonyl-3,5-diiodo-L-tyrosine, N-tert-butoxycarbonyl-O-ethyl-L-tyrosine, N-tert-butoxycarbonyl-O-ethyl-D-tyrosine, N-tert-butoxycarbonyl-O-methyl-L-tyrosine, N-tert-butoxycarbonyl-L-tyrosine, N-tert-butoxycarbonyl-D-tyrosine, N-tert-butyl-L-tyrosine tert-butyl ester-hydrochloride, N-9-fluorenylmethyloxycarbonyl-O-tert-butyl-L-tyrosine, N-9-fluorenylmethyloxycarbonyl-3,5-diiodo-L-tyrosine, N-9-fluorenylmethyloxycarbonyl-O-dimethylphospho-L-tyrosine, L-tyrosine amide, L-tyrosine allyl ester, p-toluenesulfonic acid salt, L-tyrosine benzyl ester, p-toluenesulfonic acid salt, L-tyrosine tert-butyl ester, L-tyrosine ethyl ester, L-tyrosine ethyl ester-hydrochloride, L-tyrosine methyl ester, L-tyrosine methyl ester-hydrochloride, DL-tyrosine methyl ester-hydrochloride, L-tyrosine hydrazide, DL-3-(2-hydroxyphenyl) alanine, DL-3-(3-hydroxyphenyl) alanine, Dl-o-tyrosine and DL-m-tyrosine.

The endermic liniment of the present invention contains at least one type of phenylalanine derivative and/or its salt thus obtained. The blend ratio is 0.001–20 wt % of the total amount of the endermic liniment, preferably 0.01–10 wt %, and more preferably 0.1–7 wt %. If it is less than 0.001 wt % then the skin whitening effect is insufficient. A further increase in the effect cannot be expected if more than 20 wt % is used.

The endermic liniment of the present invention can be prepared in various forms using respective conventional methods. In general, preferable forms include cream, ointment, gel, lotion, emulsion, stick, pack and solution with an organic solvent.

In addition to the aforementioned essential ingredients, the endermic liniment of the present invention, as necessary, may contain other ingredients usually used in cosmetic and medicinal endermic liniments including powders, liquid oil/fats, solid oil/fats, waxes, hydrocarbons, higher fatty acids, higher alcohols, esters, silicones, anionic surfactants, cationic surfactants, ampholytic surfactants, nonionic surfactants, humectants, water soluble polymers, thickeners, coating agents, ultraviolet light absorbents, sequestering agents, lower alcohols, polyhydric alcohols, saccharides, amino acids, organic amines, synthetic resin emulsions, pH adjusting agents, skin nutrients, vitamins, antioxidants, antioxidant assistants, perfumes and water. For these ingredients, one or more types of each can be used.

Examples of the powder ingredients are: inorganic powders including talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate, magnesium, silica, zeolite, barium sulfate, burned calcium sulfate (calcined gypsum), calcium phosphate, fluorine-apatite, hydroxyapatite, ceramic powder, metal soap (zinc myristate, calcium palmitate, aluminum stearate) and boron nitride; organic powders including polyamide resin powder (nylon powder), polyethylene powder, polymethyl methacrylate powder, polystyrene powder, styrene/acrylic acid copolymer resin powder, benzoguanamine resin powder, polyethylene tetrafluoride powder and cellulose powder; inorganic white pigments including titanium dioxide and zinc oxide; inorganic red pigments including iron oxide (red iron oxide) and iron titanate; inorganic brown pigments including γ-iron oxide; inorganic yellow pigments including yellow iron oxide and loess; inorganic black pigments including black iron oxide, carbon black and low oxides of titanium; inorganic purple pigments including mango violet and cobalt violet; inorganic green pigments including chrome oxide, chrome hydroxide and cobalt titanate; inorganic blue pigments including ultramarine blue and Berlin blue; pearl pigments including titanium oxide-coated mica, titanium oxide-coated bismuth oxychloride, titanium oxide-coated talc, colored titanium oxide-coated mica, bismuth oxychloride and fish scale flakes; metal powder pigments including aluminum powder and copper powder; organic pigments including red 201, red 202, red 204, red 205, red 220, red 226, red 228, red 405, orange 203, orange 204, yellow 205, yellow 401 and blue 404; zirconium, barium or aluminum lake organic pigments including red 3, red 104, red 106, red 227, red 230, red 401, red 505, orange 205, yellow 4, yellow 5, yellow 202, yellow 203, green 3 and blue 1; and natural colors such as chlorophyll and β-carotene. Selection is not limited to these ingredients but any powder which can be used in general cosmetics can be used.

Examples of the liquid oil/fats include avocado oil, tsubaki oil, turtle fatty acid, macademia nut oil, corn oil, mink oil, olive oil, rape seed oil, egg york oil, sesami seed oil, persic oil, wheat germ oil, sasanqua oil, castor oil, linseed oil, safflower oil, cotton seed oil, perilla oil, soy bean oil, peanut oil, tea seed oil, kaya oil, rice bran oil, chinese wood oil, Japanese wood oil, jojoba oil, germ oil, triglycerol, glyceryl trioctanoate and glyceryl triisopalmitate.

Examples of the solid oil/fats include cacao butter, coconut oil, horse tallow, hardened coconut oil, palm oil, beef tallow, sheep tallow, hardened beef tallow, palm kernel oil, pork tallow, beef bone tallow, Japanese core wax, hardened oil, neatsfoot tallow, Japanese wax and hydrogenated castor oil.

Examples of the waxes include honeybee wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether.

Examples of the hydrocarbon oils include liquid paraffin, ozokerite, squalene, pristane, paraffin, ceresin, squalene, vaseline and microcrystalline wax.

Examples of the higher fatty acids include lauric acid, myristic acid, palmitic acid, stearic acid, behenic acid, oleic acid, 12-hydroxystearic acid, undecylenic acid, tall oil (sulfated caster oil), isostearic acid, linoleic acid, linolenic acid, eicosapentaenoic acid (EPA) and docosahexaenoic acid (DHA).

Examples of the higher alcohols are: linear chain alcohols including lauryl alcohol, cetyl alcohol, stearyl alcohol, behenyl alcohol, myristyl alcohol, oleyl alcohol and cetostearyl alcohol; and branched chain alcohols including monostearylglycerol ether (batyl alcohol), 2-decyltetradecynol, lanolin alcohol, cholesterol, phytosterol, hexyldodecanol, isostearyl alcohol and octyldodecanol.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol dioctanoate, dipentaerythritol fatty acid ester, N-alkylglycol monoisostearate, neopentyl glycol dicaprylate, diisostearyl malate, glyceryl di-2-heptylundecanoate, trimethylolpropane trioctanoate, trimethylolpropane triisostearate, pentaneerythritol tetraoctanoate, glyceryl trioctanoate, trimethylolpropane triisostearate, cetyl2-ethylhexanoate, 2-ethylhexyl palmitate, glyceryl trimyristate, glyceride tri-2-heptylundecanoate, methyl castor oil fatty acid, oleyl oleate, cetostearyl alcohol, aceto glyceride, 2-heptylundecyl palmitate, diisobutyl adipate, 2-octyldodecyl n-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate.

Examples of the silicones are: chain polysiloxanes including dimethylpolysiloxane, methylphenylpolysiloxane and methylhydrogenpolysiloxane; ring polysiloxanes including decamethylpolysiloxane, dodecamethylpolysiloxane and tetramethyltetrahydrogenpolysiloxane, as well as silicone resin and silicone rubber which form three-dimensional networks.

Examples of the anionic surfactant are: fatty acid soaps including soap base, sodium laurate and sodium palmitate;

higher alkylsulfuric ester salts including sodium laurylsulfate and potassium lauryl sulfate; alkyl ether sulfuric ester salts including triethanolamine POE laurylsulfate and sodium POE laurylsulfate; n-acylsarcosinic acids including sodium lauroylsarcosinate; higher fatty acid amide sulfonates including sodium n-myristoyl-n-methyltaurate and sodium methyltaurid cocoate and sodium laurylmethyltaurid; phosphoric ester salts including sodium POE oleyl ether phosphate and POE stearyl ether phosphoric acid; sulfosuccinates including sodium di-2-ethylhexylsulfosuccinate, sodium monolauroylmonoethanolamide polyoxyethylenesulfosuccinate and sodium laurylpolypropylene glycol sulfosuccinate; alkylbenzenesulfonates including sodium linear dodecylbenzenesulfonate, triethanolamine linear dodecylbenzenesulfonate and linear dodecylbenzenesulfonic acid; n-acylglutamates including monosodium n-lauroylglutamate, disodium n-stearoylglutamate and monosodium n-myristoyl-L-glutamate; higher fatty acid sulfates including sodium hydrogenated glyceryl cocoate sulfate; sulfated oils including turkey red oil; as well as POE alkyl ether carbonate, POE alkylaryl ether carbonate, α-olefinsulfonates, higher fatty acid ester sulfonate, sec-alcohol sulfate, higher fatty acid alkyl amide sulfate, sodium lauroyl monoethanolamine succinate, ditriethanolamine n-palmitoylaspartate and sodium caseinate.

Examples of the cationic surfactants are: alkyltrimethyl ammonium salts including stearyltrimethyl ammonium chloride and lauryltrimethyl ammonium chloride; distearyl dimethyl ammonium chloride/dialkyl dimethyl ammonium chloride; alkylpyridinium salts including poly (N,N-dimethyl-3,5-methylene pyridinium chloride) and cetyl pyridinium chloride; as well as tetra alkyl ammonium salt, alkyldimethylbenzyl ammonium salt, alkylisoquinolinium salt, dialkylmorpholine salt, POE alkylamine, alkylamine salt, polyamine fatty acid derivatives, amylalcohol fatty acid derivatives, benzalkonium chloride and benzetonium chloride.

Examples of the ampholytic surfactants are imidazoline type ampholytic surfactants including 2-undecyl-N,N,N-(hydroxyethylcarboxymethyl)-2-imidazoline sodium salt and 2-cocoyl-2-imidazaliniumhydroxide-1-carboxyethyloxy 2 sodium salt and betaine type surfactants including 2-heptadecyl-n-carboxymethyl-n-hydroxyethyl imidazolinium betaine, betaine lauryldimethylamino acetate, alkyl betaine, amide betaine and sulfobetaine.

Examples of the lipophilic non-ionic surfactants are: sorbitan fatty acid esters including sorbitan monooleate, sorbitan monoisostearate, sorbitan monolaurate, sorbitan monopalmitate, sorbitan monostearate, sorbitan sesquioleate, sorbitan trioleate, diglycerolsorbitan pentaoctanoate and diglycerolsorbitan tetraoctanoate; glycerol polyglycerol fatty acids including mono-cottonseed-fatty acid glyceryl ester, glyceryl monoerucate, glyceryl monostearate, glyceryl α, α'-oleate pyroglutamate and glyceryl monostearate monomalate; propylene glycol fatty acid esters including propylene glycol monostearate, as well as hydrogenated castor oil derivatives and glycerol alkyl ether.

Examples of the hydrophilic non-ionic surfactants are: POE sorbitan fatty acid esters including POE-sorbitan monooleate, POE-sorbitan monostearate, POE-sorbitan monoolate and POE-sorbitan tetraoleate; POE-sorbitol fatty acid esters including POE-sorbitol monolaurate, POE-sorbitol monooleate, POE-sorbitol pentaoleate and POE-sorbitol monostearate; POE-glycerol fatty acid esters including POE-glyceryl monostearate, POE-glyceryl monoisostearate and POE-glyceryl triisostearate; POE fatty acid esters including POE monooleate, POE distearate, POE monodioleate and ethylene glycol cysteaphosphate; POE alkyl ethers including POE lauryl ether, POE oleyl ether, POE stearyl ether, POE behenyl ether, POE2-octyldodecyl ether and POE cholestanol ether; POE alkylphenyl ethers including POE octylphenyl ether, POE nonylphenylether and POE dinonylphenyl ether; pluaronics including pluronic; POE-POP alkyl ethers including POE-POP cetyl ether, POE-POP2-decyltetradecyl ether, POE-POP monobutyl ether, POE-POP lanolin hydrate and POE-POP glycerol ether; tetra POE-tetra POP ethylenediamine condensates including tetronic; POE castor oil hydrogenated castor oil derivatives including POE castor oil, POE hydrogenated castor oil, POE hydrogenated castor oil monoisostearate, POE hydrogenated castor oil triisostearate, POE hydrogenated castor oil monopyroglutamate monoisostearate, POE hydrogenated castor oil maleate; POE honeybee wax/lanolin derivatives including POE sorbitol honey bee; alkanol amides including coconut fatty acid diethanol amide, lauric acid monoethanol amide and fatty acid iropropanol amide; as well as POE propylene glycol fatty acid ester, POE alkyl amine, POE fatty acid amide, sucrose fatty acid ester, POE nonylphenylformaldehyde condensate, alkylethoxydimethylamine oxide and trioleyl phosphate.

Examples of the humectants include polyethylene glycol, propylene glycol, glycerol, 1,3-butylene glycol, xylitol, sorbitol, maltitol, chondroitin sulfuric acid, hyaluronic acid, mucoitin sulfuric acid, charonic acid, water-soluble collagen solution, cholesteryl-12-hydroxystearate, sodium lactate, bile acid salt, dl-pyrolidonecarbonate, short-chain soluble collagen, diglycerol (EO)PO adduct extract, yerrow extract and sweet clover extract.

Examples of the natural water soluble polymers are: plant polymers including gum arabic, gum tragacanth, galactan, guar gum, carob gum, karaya gum, carrageenan, pectin, agar, quince seed, algae colloid (brown algae extract), starch (rice, corn, potato, wheat) and glycyrrhizic acid; microbial polymers including xanthangum, dextran, succinoglucane and pullulan; and animal polymers including collagen, casein, albumin and gelatin.

Examples of the semi-synthesized water soluble polymers are: starch type polymers including carboxymethyl starch and methylhydroxypropyl starch; cellulose type polymers including methyl cellulose, nitro cellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose and cellulose powder; alginic acid type polymers including sodium alginate and propyleneglycol alginate ester.

Examples of the synthesized water soluble polymers are: vinyl type polymers including polyvinyl alcohol, polyvinylmethyl ether, polyvinyl pyrolidone and carboxyvinyl polymer (carbopol); polyoxyethylene type polymers including polyethylene glycol 20,000, 4,000,000 and 600,000; polyoxyethylene polyoxypropylene copolymer copolymerization type polymer; acrylic polymers including sodium polyacrylate, polyethyl acrylate and polyacryl amide; as well as polyethylene imine and cation polymer.

Examples of the inorganic water soluble polymers include bentonite, AlMg silicate (beegum), laponite, hectorite and anhydrous silicic acid.

Examples of the thickeners include gum arabic, carrageenan, karaya gum, gum tragacanth, carob gum, quince seed, casein, dextrine, gelatin, sodium pectate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, cellulose dialkylmethyl ammonium sulfate, xanthangum, aluminum magnesium silicate, bentonite and hectorite.

Examples of the ultraviolet light absorbents are: benzoic acid type ultraviolet light absorbents including para-amino benzoic acid (hereafter abbreviated as PABA), PABA monoglycerol ester, N,N-dipropoxy PABA ethyl ester, N,N-diethoxy PABA ethyl ester, N,N-dimethyl PABA ethyl ester, N,N-dimethyl PABA butyl ester and N,N-dimethyl PABA ethyl ester; anthranilic acid type ultraviolet light absorbents including homomentyl-N-acetyl anthranilate; salicylic acid type ultraviolet light absorbents including amyl salicylate, mentyl salicylate, homomentyl salicylate, octyl salicylate, phenyl salicylate, benzyl salicylate and p-isopropanolphenyl salicylate; cinnamic acid type ultraviolet light absorbents including octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glyceryl mono-2-ethylhexanoyl-diparamethoxy cinnamate; benzophenone type ultraviolet light absorbents including 2,4-dihydroxy benzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone and 4-hydroxy-3-carboxy benzophenone; as well as 3-(4'-methylbenzylidene)-d,l-camphor, 3-benzylidene-d,l-camphor, urocanic acid, ethyl urocanate, 2-phenyl-5-methyl benzoxazol, 2,2'-hydroxy-5-methylphenyl benzotriazol, 2-(2'-hydroxy-5'-t-octylphenyl) benzotriazol, 2-(2'-hydroxy-5'-methylphenyl benzotriazol, dibenzaladine, dianisoylmethane, 4-methoxy-4'-t-butyldibenzoylmethane and 5-(3,3-dimethyl-2-norbornylidene)-3-pentane-2-one. By adding ultraviolet light absorbing substances including these ultraviolet light absorbents and various plant extracts and such which have an ultraviolet light absorbing action, the endermic liniment can be endowed with both sunburn prevention effects and curing effects.

Examples of the sequestering agent include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, malic acid, citric acid, ascorbic acid, succinic acid and edetic acid.

Examples of the lower alcohols include methanol, ethanol, propanol, isopropanol, isobutyl alcohol and t-butyl alcohol.

Examples of the polyhydric alcohols are: dihydric alcohols including ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; trihydric alcohols including glycerol, trimethylolpropane and 1,2,6-hexanetriol; tetrahydric alcohols including pentaerythritol; pentahydric alcohols including xylitol; hexahydric alcohols including sorbitol and mannitol; polyhydric alcohol polymers including diethylene glycol, dipropylene glycol, triethylene glycol, polypropylene glycol, triglycerol, tetraglycerol and poly glycerol; dihydric alcohol alkyl ethers including ethylene glycol monomethyl ether, ethylene glycol monoethyl ether, ethylene glycol monobutyl ether, ethylene glycol monophenyl ether, ethylene glycol monohexyl ether, ethylene glycol mono2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibuthyl ether; dihydric alcohol alkyl ethers including diethylene glycol monometyl ether, diethylene glycol monoetyl ether, diethylene glycol monobutyl ether, diethylene glycol dimetyl ether, diethylene glycol dietyl ether, diethylene glycol dibutyl ether, diethylene glycol methylethyl ether, triethylene glycol monometyl ether, triethylene glycol monoetyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether; dihydric alcohol ether ester including ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate; glycerol monoalkyl ethers including xylyl alcohol, selachyl alcohol and batyl alcohol; sugar alcohols including sorbitol, maltitol, maltotriose, mannitol, sucrose, erythritol, glucose, fructose, starch amylolysis sugar, maltose, xylitose and alcohol prepared by reducing starch amyolysis sugar; as well as glysolid, tetrahydrofurfuryl alcohol, POE tetrahydrofurfuryl alcohol, POP butyl ether, POP POE butyl ether, tripolyoxypropylene glycerol ether, POP glycerol ether, POP glycerol ether phosphoric acid and POP POE pentaneerythritol ether.

Examples of the monosaccharides are: trioses including D-glyceryl aldehyde and dihydroxy acetone; tetroses including D-erythrose, D-erythrulose, D-threose and erythritol; pentoses including L-arabinose, D-xylose, L-lyxose, D-arabinose, D-ribose, D-ribulose, D-xylulose and L-xylulose; hexoses including D-glucose, D-talose, D-psicose, D-galactose, D-fructose, L-galactose, L-mannose and D-tagatose; heptoses including aldoheptose and hepturose; octoses including octurose; deoxy sugars including 2-deoxy-D-ribose, 6-deoxy-L-galactose and 6-deoxy-L-mannose; amino sugars including D-glucosamine, D-galactosamine, sailic acid, aminouronic acid and muramic acid; uronic acids including D-glucuronic acid, D-mannuronic acid, L-gulonic acid, D-galacturonic acid and L-iduronic acid.

Examples of the oligosaccharides include sucrose, gunchianose, umbelliferose, lactose, planteose, isolignoses, α, α-trehalose, raffinose, lignoses, umbilicine, stachyose and belbascose.

Examples of the polysaccharides include cellulose, quince seed, chondroitin sulfuric acid, starch, galactan, dermatan sulfate, glycogen, gum arabic, heparan sulfate, hyaluronic acid, gum tragacanth, keratan sulfate, chondroitin, xanthan gum, mucoitin sulfuric acid, guar gum, dextran, kerato sulfate, locust bean gum, succinoglucane and charonic acid.

Examples of the amino acids are: neutral amino acids including glycine, alanine, valine, leucine, isoleucine, serine, threonine, tryptophane, cystine, cysteine, methionine, proline and hydroxyproline: acidic amino acids including aspartic acid, glutamic acid, asparagine and glutamine: basic amino acids including arginine, histidine, lysine and hydroxylysine.

Examples of the amino acid derivatives include sodium acyl sarcosinate (sodium N-lauroyl sarcosinate), acyl glutaminate, sodium acyl β-alanine, glutathione and pyrolidonecarboxylic acid.

Examples of the organic amines include monoethanol amine, diethanol amine, triethanol amine, morpholine, triisopropanol amine, 2-amino-2-methyl-1,3-propanediol and 2-amino-2-methyl-1-propanol.

Examples of the synthetic resin emulsions include acrylic resin emulsion, polyethyl acrylate emulsion, acrylic resin liquid, polyacrylalkyl ester emulsion and polyvinyl acetate resin emulsion.

Examples of the pH adjusting agents include buffers such as lactic acid-sodium lactate and citric acid-sodium citrate.

Examples of the vitamins include vitamins A, B1, B2, B6 and E, as well as their derivatives, pantothenic acid and its derivatives and biotin.

Examples of the antioxidants include tocopherols, dibutylhydroxytoluene, butylhydroxyanisole and gallic acid esters.

Examples of the antioxidant assistants include phosphoric acid, citric acid, ascorbic acid, maleic acid, malonic acid, succinic acid, fumaric acid, cephalin, hexametaphosphate, phytic acid and ethylenediamine-tetraacetic acid.

EXAMPLES

The present invention is described in detail below by referring to examples. The present invention is not limited to these examples. The blend ratio is indicated in wt % unit. Prior to the examples, methods of testing and evaluating the effects of the present invention are described.

Whitening Effect Test 1

Testing Method

Weiser Maple guinea pigs with phototoxic pigmentation, treated with 8-methoxypsoralen, were used. 50 microliters of each sample was applied on an approximately 4 cm$^2$ area on the shaved back once a day for 8 weeks. Decoloration of the pigmentation and pigmentation enhancement which occurred as a side effect were evaluated using a 4-point evaluation method (+ stands for decoloration and − stands for the side effect). 5 animals constituted one group. The testing was conducted for the samples from Examples 1–5 and Comparative Examples 1–4 described below.

Evaluation Method

For each sample, the average evaluation points of 5 animals after 8 weeks were determined based on the following assessment criteria.

Assessment Criteria

Decoloration of the Pigmentation (3 points): The pigmentation had become almost imperceptible.

(2 points): The pigmentation had become very faint.

(1 point): The pigmentation had become fainter.

(0 point): No change was observed.

Enhancement of the Pigmentation (side effects)

(0 point): No change was observed.

(−1 point): The pigmentation had become somewhat darker.

(−2 point): The pigmentation had become darker.

(−3 point): The pigmentation had become very dark.

Sample for Examples 1–5 and Comparative Examples 1–4:

|  | wt % |
|---|---|
| Alcohol phase |  |
| 95% ethyl alcohol | 25.0 |
| Polyoxyethylene (25 mol) hydrogenated castor oil ether | 2.0 |
| Antioxidant, preservative | Appropriate amount |
| Perfume | Appropriate amount |
| Drug (drug listed in Table 1) | 1.0 |
| Water phase |  |
| Glycerol | 5.0 |
| Sodium hexametaphosphate | Appropriate amount |
| Ion exchanged water | Balance |

Preparation Method

The water phase and the alcohol phase were prepared and solubilized.

TABLE 1

|  | Drug (chemical name) |
|---|---|
| Example 1 | N-benzyloxycarbonyl-L-tyrosine |
| Example 2 | DL-o-tyrosine |
| Example 3 | O-benzyl-L-tyrosine |
| Example 4 | N-acetyl-L-tyrosine amide |
| Example 5 | L-tyrosine amide hydrochloride |
| Comparative Example 1 | Hydroquinone |
| Comparative Example 2 | D,L-β-methylphenylalanine |
| Comparative Example 3 | α-methyltyrosine |
| Comparative Exampie 4 | L-tyrosinol hydrochloride |

As is clearly shown in Table 2 below, the Examples compared with the Comparative Examples, showed superior pigmentation decoloration effect on Weiser Maple guinea pigs with phototoxic pigmentation, treated with 8-methoxypsoralen.

TABLE 2

|  | Average Evaluation Points After 8 Weeks |
|---|---|
| Example 1 | 2.0 |
| Example 2 | 1.9 |
| Example 3 | 2.2 |
| Example 4 | 2.1 |
| Example 5 | 1.8 |
| Comparative Example 1 | 0.5 |
| Comparative Example 2 | 0.5 |
| Comparative Example 3 | 0.5 |
| Comparative Example 4 | 0.5 |

Whitening Effect Test 2

Testing Method

Ninety subjects were exposed to the summer sunlight for 4 hours (2 hours a day for 2 days) and each sample was applied on the skin on the inner side of their upper arm once in the morning and once in the evening for 8 weeks beginning 5 days after they were exposed to the sunlight. The panel was divided into 9 groups, each of which had 10 subjects. The testing was conducted using each sample from Examples 1–5 and Comparative Examples 1–4.

Evaluation Method

The hypochromic effect after the use of the samples was evaluated based on the assessment criteria described below.

Assessment Criteria

Very effective: The pigmentation had become almost imperceptible.

Effective: The pigmentation had become very faint.
Somewhat effective: The pigmentation had become fainter.
Not effective: No change was observed.

Assessment

◉: 80% or more of the subjects tested "very effective" or "effective".

○: 50–80% of the subjects tested "very effective" or "effective".

Δ: 30–50% of the subjects tested "very effective" or "effective".

X: 30% or less of the subjects tested "very effective" or "effective".

As is clearly shown in Table 3 below, the Examples had a superior whitening effect after exposure to the sun light, i.e. prevention of skin darkening by preventing deposition of melanin pigment, compared with the Comparative Examples.

TABLE 3

| Whitening Effect | |
| --- | --- |
| Example 1 | ◉ |
| Example 2 | ◉ |
| Example 3 | ◉ |
| Example 4 | ◉ |
| Example 5 | ◉ |
| Comparative Example 1 | Δ |
| Comparative Example 2 | Δ |
| Comparative Example 3 | Δ |
| Comparative Example 4 | Δ |

Whitening Effect Test 3

Testing Method 180 people who were suffering from dark skin, chloasma, freckles, etc. were chosen as the subjects. Each sample was applied on their faces everyday for three months. The panel was divided into 9 groups, each of which had 20 subjects. The testing was conducted using each sample from Examples 1–5 and Comparative Examples 1–4.

Evaluation Method

The hypochromic effect after three months was evaluated based on the assessment criteria described below.

Assessment Criteria

Very effective: The pigmentation had become almost imperceptible.
Effective: The pigmentation had become very faint.
Somewhat effective: The pigmentation had become fainter.
Not effective: No change was observed.

Assessment

◉: 80% or more of the subjects tested "very effective" or "effective".

○: 50–80% of the subjects tested "very effective" or "effective".

Δ: 30–50% of the subjects tested "very effective" or "effective".

X: 30% or less of the subjects tested "very effective" or "effective".

As is clearly shown in Table 4, the Examples had a superior whitening effect against dark skin, chloasma, freckles, etc. compared with the Comparative Examples.

TABLE 4

| Whitening Effect | |
| --- | --- |
| Example 1 | ◉ |
| Example 2 | ◉ |
| Example 3 | ◉ |
| Example 4 | ◉ |
| Example 5 | ◉ |
| Comparative Example 1 | Δ |
| Comparative Example 2 | Δ |
| Comparative Example 3 | Δ |
| Comparative Example 4 | Δ |

Example 6

| Cream | wt % |
| --- | --- |
| Stearic acid | 5.0 |
| Stearyl alcohol | 4.0 |
| Isopropyl myristate | 18.0 |
| Glyceryl monostearate | 3.0 |
| Propylene glycol | 10.0 |
| N-acetyl-L-tyrosine ethyl ester | 20.0 |
| Caustic potash | 0.2 |
| Sodium hydrogen sulfite | 0.01 |
| Preservative | Appropriate amount |
| Ion exchanged water | Balance |

Preparation Method

Propylene glycol and caustic potash were added to the ion exchanged water and the temperature was raised to and maintained at 70° C. (water phase). Other ingredients were mixed in and heat-melted, and the temperature was maintained at 70° C. (oil phase). The oil phase was gradually added to the water phase. After all the oil phase was added, the temperature was maintained for a while to allow the reaction to occur. The system was then homogeneously emulsified using a homo-mixer and cooled down to 30° C. while being thoroughly stirred.

Example 7

| Cream | wt % |
| --- | --- |
| Stearic acid | 6.0 |
| Sorbitan monostearate | 2.0 |
| Polyoxyethylene (20 mol) sorbitan monostearate | 1.5 |
| Propylene glycol | 10.0 |
| O-benzyl-L-tyrosine | 7.0 |
| Glyceryl octanoate | 10.0 |
| Squalene | 5.0 |
| Sodium hydrogen sulfite | 0.01 |
| Ethyl paraben | 0.3 |
| Preservative | Appropriate amount |
| Ion exchanged water | Balance |

Preparation Method

Propylene glycol was added to the ion exchanged water and the temperature was raised to and maintained at 70° C. (water phase). Other ingredients were mixed in and heat-melted, and the temperature was maintained at 70° C. (oil phase). The oil phase was added to the water phase. After pre-emulsification, the system was homogeneously emulsified using a homo-mixer and cooled down to 30° C. while being thoroughly stirred.

Example 8

| Cream | wt % |
| --- | --- |
| Stearyl alcohol | 7.0 |
| Stearic acid | 2.0 |
| Lanolin hydrate | 2.0 |
| Squalene | 5.0 |
| 2-octyldodecyl alcohol | 6.0 |
| Polyoxyethylene (25 mol) cetyl alcohol ether | 3.0 |
| Glyceryl monostearate | 2.0 |
| Propylene glycol | 5.0 |
| DL-o-tyrosine | 0.001 |
| Perfume | Appropriate amount |
| Sodium hydrogen sulfite | 0.03 |
| Ethyl paraben | 0.3 |
| Ion exchanged water | Balance |

Preparation Method

Propylene glycol was added to the ion exchanged water and the temperature was raised to and maintained at 70° C. (water phase). Other ingredients were mixed in and heat-melted, and the temperature was maintained at 70° C. (oil phase). The oil phase was added to the water phase. After pre-emulsification, the system was homogeneously emulsified using a homo-mixer and cooled down to 30° C. while being thoroughly stirred.

Example 9

| Emulsion | wt % |
| --- | --- |
| Stearic acid | 2.5 |
| Cetyl alcohol | 1.5 |
| Vaseline | 5.0 |
| Liquid paraffin | 10.0 |
| Polyoxyethylene (10 mol) monooleate | 2.0 |
| Propylene glycol 1500 | 5.0 |
| Triethanol amine | 1.0 |
| L-tyrosine β-naphtyl amide | 10.0 |
| Sodium hydrogen sulfite | 0.01 |
| Ethyl paraben | 0.3 |
| Carboxyvinyl polymer | 0.05 |
| Perfume | Appropriate amount |
| Ion exchanged water | Balance |

Preparation Method

Carboxyvinyl polymer was dissolved in a small amount of ion exchanged water (A phase). Propylene glycol 1500 and triethanol amine were added to the rest of the ion exchanged water and heat-dissolved, and the temperature was maintained at 70° C. (water phase). Other ingredients were mixed in and heat-melted, and the temperature was maintained at 70° C. (oil phase). The oil phase was added to the water phase. After pre-emulsification, A phase was added and the system was homogeneously emulsified using a homo-mixer and cooled down to 30° C. while being thoroughly stirred.

Example 10

| Emulsion | wt % |
| --- | --- |
| Oil Phase: | |
| Stearyl alcohol | 1.5 |
| Squalene | 2.0 |
| Vaseline | 2.5 |
| Deodorized liquid lanolin | 1.5 |
| Evening primrose oil | 2.0 |
| Isopropyl myristate | 5.0 |
| Glyceryl monooleate | 2.0 |
| Polyoxyethylene (60 mol) hydrogenated castor oil | 2.0 |
| Tocopherol acetate | 0.05 |
| Ethyl paraben | 0.2 |
| Butyl paraben | 0.1 |
| L-tyrosine amide hydrochloride | 1.0 |
| N-tert-butoxycarbonyl-O-methyl-L-tyrosine | 1.0 |
| Perfume | Appropriate amount |
| Water Phase: | |
| Sodium hydrogen sulfite | 0.01 |
| Glycerol | 5.0 |
| Sodium hyaluronate | 0.01 |
| Carboxyvinyl polymer | 0.2 |
| Potassium hydroxide | 0.2 |
| Purified water | Balance |

Preparation Method

The oil phase was dissolved at 70° C. The water phase was dissolved at 70° C. The oil phase was mixed into the water phase and emulsification was conducted using an emulsifier. The temperature was then lowered down to 30° C. using a heat exchanger.

Example 11

| Jelly | wt % |
| --- | --- |
| 95% ethyl alcohol | 10.0 |
| Dipropylene glycol | 15.0 |
| Polyoxyethylene (50 mol) oleyl alcohol ether | 2.0 |
| Carboxyvinyl polymer | 1.0 |
| Caustic soda | 0.15 |
| L-arginine | 0.1 |
| N-acetyl-L-tyrosine amide | 1.0 |
| L-tyrosine hydrazide | 1.0 |
| Methyl paraben | 0.2 |
| Perfume | Appropriate amount |
| Ion exchanged water | Balance |

Preparation Method

Carboxyvinyl polymer was homogeneously dissolved in the ion exchanged water. N-acetyl-L-tyrosine amide, L-tyrosine hydrazide and polyoxyethylene (50 mol) oleyl alcohol ether were dissloved in the 95 % ethanol and this was added to the water phase. After other ingredients were added, the system was neutralized and thickened by adding caustic soda and L-arginine.

Example 12

| Essence | wt % |
| --- | --- |
| A Phase: | |
| Ethanol (95%) | 10.0 |
| Polyoxyethylene (20 mol) octyldodecanol | 1.0 |
| Methyl paraben | 0.15 |
| Pantothenylethyl ether | 0.1 |
| N-9-fluorenylmethyloxycarbonyl-L-tyrosine | 0.05 |
| B Phase: | |
| Potassium hydroxide | 0.1 |
| C Phase: | |
| Glycerol | 5.0 |
| Dipropylene glycol | 10.0 |

-continued

| Essence | wt % |
| --- | --- |
| Sodium hydrogen sulfite | 0.03 |
| Carboxyvinyl polymer | 0.2 |
| Purified water | Balance |

Preparation Method

Each A phase and C phase was homogeneously dissolved, and the A phase was added to the C phase, followed by solubilization. The B phase was then added and the system was filled into a container.

Example 13

| Pack | | wt % |
| --- | --- | --- |
| A Phase: | | |
| | Dipropylene glycol | 5.0 |
| | Polyoxyethylene (60 mol) hydrogenated castor oil | 5.0 |
| B Phase: | | |
| | N-tert-butoxycarbonyl-O-ethyl-D-tyrosine | 1.0 |
| | L-tyrosine ethyl ester hydrochloride | 1.0 |
| | Olive oil | 5.0 |
| | Tocopherol acetate | 0.2 |
| | Ethyl paraben | 0.2 |
| | Perfume | 0.2 |
| C Phase: | | |
| | Sodium hydrogen sulfite | 0.03 |
| | Polyvinyl alcohol (degree of saponification 90, degree of polymerization-2,000) | 13.0 |
| | Ethanol | 7.0 |
| | Purified water | Balance |

Preparation Method

A phase, B phase and C phase were homogeneously dissolved, and the B phase was added to the A phase, followed by solubilization. The C phase was then added and the system was filled into a container.

All of the endermic liniments obtained in the present invention were found effective in the whitening effect tests conducted for Examples 1–5.

What is claimed is:

1. An endermic liniment containing at least one type of phenylalanine compound selected from the group consisting of N-benzyloxycarbonyl-L-tyrosine, N-benzyloxycarbonyl-D-tyrosine, N-benzoyl-L-tyrosine, N-benzoyl-D-tyrosine, N-(p-methoxybenzoyl)-L-tyrosine, N-(p-methoxybenzoyl)-D-tyrosine, N-(p-hydroxybenzoyl)-L-tyrosine, N-(p-hydroxybenzoyl)-D-tyrosine, O-benzyloxycarbonyl-L-tyrosine, N-benzyloxycarbonyl-L-tyrosine hydrazide, N-acetyl-L-tyrosine hydrazide, N-acetyl-L-tyrosine amide, 4-methoxy-L-phenylalanine, 4-methoxy-L-phenylalanine hydrochloride, 4-methoxy-DL-phenylalanine, N-benzyloxycarbonyl-O-benzyl-L-tyrosine, O-benzyl-L-tyrosine, O-phospho-L-tyrosine, O-phospho-DL-tyrosine, O-phospho-D-tyrosine, L-tyrosine β-naphthyl amide, N-tert-butoxycarbonyl-L-3,4-dihydroxyphenylalanine, N-tert-butoxycarbonyl-O-acetyl-L-tyrosine, N-tert-butoxycarbonyl-O-acetyl-D-tyrosine, N-tert-butoxycarbonyl-3,5-diiodo-L-tyrosine, N-tert-butoxycarbonyl-O-ethyl-L-tyrosine, N-tert-butoxycarbonyl-O-ethyl-D-tyrosine, N-tert-butoxycarbonyl-O-methyl-L-tyrosine, N-tert-butoxycarbonyl-L-tyrosine, N-tert-butoxycarbonyl-D-tyrosine, N-9-fluorenylmethyloxycarbonyl-O-tert-butyl-L-tyrosine, N-9-fluorenylmethyloxycarbonyl-3,5-diiodo-L-tyrosine, N-9-fluorenylmethyloxycarbonyl-O-dimethylphospho-L-tyrosine, L-tyrosine amide, L-tyrosine hydrazide, DL-3-(2-hydroxyphenyl) alanine, and DL-o-tyrosine.

2. A method of bleaching skin comprising applying to the skin at least one type of compound selected from the group consisting of N-benzyloxycarbonyl-L-tyrosine, N-benzyloxycarbonyl-D-tyrosine, N-benzoyl-L-tyrosine, N-benzoyl-D-tyrosine, N-(p-methoxybenzoyl)-L-tyrosine, N-(p-methoxybenzoyl)-D-tyrosine, N-(p-hydroxybenzoyl)-L-tyrosine, N-(p-hydroxybenzoyl)-D-tyrosine, O-benzyloxycarbonyl-L-tyrosine, N-benzyloxycarbonyl-L-tyrosine hydrazide, N-acetyl-L-tyrosine hydrazide, N-acetyl-L-tyrosine amide, 4-methoxy-L-phenylalanine, 4-methoxy-L-phenylalanine hydrochloride, 4-methoxy-DL-phenylalanine, N-benzyloxycarbonyl-O-benzyl-L-tyrosine, O-benzyl-L-tyrosine, O-phospho-L-tyrosine, O-phospho-DL-tyrosine, O-phospho-D-tyrosine, L-tyrosine β-naphthyl amide, N-tert-butoxycarbonyl-L-3,4-dihydroxyphenylalanine, N-tert-butoxycarbonyl-O-acetyl-L-tyrosine, N-tert-butoxycarbonyl-O-acetyl-D-tyrosine, N-tert-butoxycarbonyl-3,5-diiodo-L-tyrosine, N-tert-butoxycarbonyl-O-ethyl-L-tyrosine, N-tert-butoxycarbonyl-O-ethyl-D-tyrosine, N-tert-butoxycarbonyl-O-methyl-L-tyrosine, N-tert-butoxycarbonyl-L-tyrosine, N-tert-butoxycarbonyl-D-tyrosine, N-9-fluorenylmethyloxycarbonyl-O-tert-butyl-L-tyrosine, N-9-fluorenylmethyloxycarbonyl-3,5-diiodo-L-tyrosine, N-9-fluorenylmethyloxycarbonyl-O-dimethylphospho-L-tyrosine, L-tyrosine amide, L-tyrosine hydrazide, DL-3-(2-hydroxyphenyl) alanine, and DL-o-tyrosine.

* * * * *